United States Patent [19]

Marcus

[11] 4,368,138
[45] Jan. 11, 1983

[54] WATER SOLUBLE THYMIDINE DERIVATIVE

[76] Inventor: Israel Marcus, 25 Washington St., Jerusalem, Israel

[21] Appl. No.: 110,397

[22] Filed: Jan. 8, 1980

[30] Foreign Application Priority Data

Jan. 10, 1979 [GB] United Kingdom ................. 7900893

[51] Int. Cl.$^3$ .................. B01F 3/18; A01N 31/14; A61K 31/70; A61K 31/505
[52] U.S. Cl. .................. 252/363.5; 424/1; 424/180; 424/251
[58] Field of Search .................. 252/363.5; 424/180, 424/251; 562/457

[56] References Cited

U.S. PATENT DOCUMENTS

| | | | |
|---|---|---|---|
| 2,441,341 | 5/1948 | Vitalis | 252/363.5 X |
| 2,949,449 | 8/1960 | Hoffer | 424/180 X |
| 3,320,236 | 5/1967 | Collins et al. | 424/180 X |
| 3,579,453 | 5/1971 | Dupre et al. | 252/356 X |

*Primary Examiner*—Richard D. Lovering
*Attorney, Agent, or Firm*—Rogers, Eilers & Howell

[57] ABSTRACT

Thymidine may have its solubility in water increased by as much as 10 times or even more by combining the thymidine with a solubilizing agent, such as a salicylate derivative selected from salicylic acid, amino and methyleneamino substituted salicylic acids and salts and esters thereof. The thymidine and solubilizing agent may be combined by grinding in the dry state. The compounds are most conveniently used in approximately equimolar quantities.

19 Claims, No Drawings

WATER SOLUBLE THYMIDINE DERIVATIVE

BACKGROUND AND SUMMARY OF THE INVENTION

The present invention relates to a form of the drug thymidine having an increased solubility.

Thymidine, whose systematic name is 1-(2-deoxy-βD-ribofuranosyl)-5-methyluracil, is a constituent of deoxyribonucleic acid and may be isolated from thymonucleic acid. It has the structure:

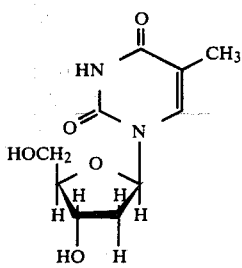

Thymidine may be used to reverse, at least partially, the systemic effects of idoxuridine. Thymidine is also used as a bioassay and metabolic reagent, as a tagged carrier of radioactive tritium. Recently interest in the pharmaceutical uses of thymidine has increased, principally as an anti-cancer agent. However, investigation and use of thymidine have been hampered by its relatively low solubility in water. Although thymidine is reported in the literature to be water-soluble, this solubility is too low for many practical purposes and hampers its use. For example, in order adequately to investigate the anti-cancer activity of thymidine in aqueous solution, it would be necessary to inject some 20 liters of the aqueous solution into the patient, a quantity which is clearly unacceptable. Use of thymidine for other purposes is also enhanced by increasing its solubility, for example by requiring a smaller volume of solution.

We have now discovered a method of enhancing the water-solubility of thymidine. Thus, in its broadest aspect, the present invention provides a water-soluble form of thymidine and solutions thereof.

Surprisingly, we have found that the presence of a solubilizing agent significantly enhances the water-solubility of thymidine. Thus, the invention further consists in a composition of thymidine and a solubilizing agent and solutions of the same.

We have found that suitable solubilizing agents are salicylic acid and derivatives thereof. Preferred derivatives are amino- and methyleneamino-substituted salicylic acids. Since the administration of acidic substances for therapeutic purposes is not normally desired, it is preferred to employ the salicylic acid or derivative thereof in the form of a salt or ester. The salt is preferably an alkali metal salt, most preferably the sodium salt.

Although, as will be demonstrated hereafter, a wide range of salicylic acid derivatives has been found to be effective in the solubilization of thymidine, we prefer to employ p-methyleneaminosalicylic acid or a salt or ester thereof, in view both of their excellent solubilizing effect and their lack of side reactions in the human body. Thus, although the solubilizing effect of sodium p-aminosalicylate is as good as, or possibly better than, the solubilizing effect of sodium p-methyleneaminosalicylate, it has been suggested that sodium p-aminosalicylate may have untoward side effects, whereas sodium p-methyleneaminosalicylate has been proven safe and is thus better for general therapeutic use. On the other hand, of course, in the case of a critical cancer patient, minor side effects brought upon by sodium p-aminosalicylate may be of little practical importance.

The manner in which the two ingredients of the composition are combined may have some effect on the activity of the resulting composition and, surprisingly, I have found that the best results are achieved simply by grinding together the powders of thymidine and the solubilizing agent, especially the salicylic acid derivative. It is possible to react the thymidine and the solubilizing agent together in a suitable common solvent (e.g. methanol) and then to evaporate off the solvent to leave a solid residue. This solid residue has good water solubility but, despite carrying out this reaction under a number of different conditions, I have found that the reaction product has a therapeutic activity rather less than that of the parent thymidine, for some purposes. However, where the identical chemical activity of thymidine is not required, such a product may be used. By simply grinding together the two components, the whole of the original chemical activity of the thymidine is retained, and water solubility is increased.

It is also possible, of course, to dissolve the two ingredients of the composition (the thymidine and the solubilizing agent) in the aqueous medium in which they are to be administered to the patient and, in such a case, it is believed that the full activity of the thymidine is retained. However, for commercial purposes, it is not desirable that the ingredients should be dissolved in the aqueous medium too far in advance of administration, nor is it desirable that the separate ingredients should be supplied to the practitioner, since this could give rise to dosage errors. For this reason, for commercial purposes, the best form of the composition of the invention is that produced by grinding together the two dry powders.

Because of the way in which the composition of the invention is prepared, the exact form of liaison or interaction between the two components of the composition is unclear. It seems unlikely in the first instance, at least, that the mere grinding together of the two powders would provide any form of chemical bonding and it is, therefore, possible that the composition is a simple mixture of the two components. This concept may be supported by the fact that bringing the two components together under conditions where they would be expected to undergo some form of chemical reaction (i.e. in the presence of a good reaction solvent, such as methanol) leads to a loss of therapeutic activity, possibly as the result of freezing the structure of thymidine (which is normally believed to exist in the form of a number of tautomers) into an inactive or less active form, e.g. as follows:

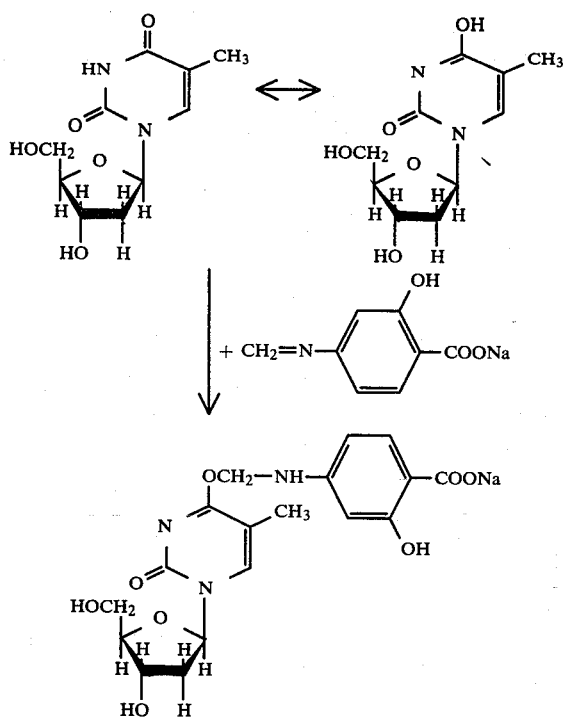

Moreover, throughout all of the experiments described in the following Examples, the starting materials could be identified unchanged on silica gel thin layer chromatography plates eluted with 2-propanol, thus suggesting that the complex, if, indeed, it is a complex, between the thymidine and the solubilizing agent is extremely labile and suggesting very strongly the absence of any covalent bonds between the two ingredients. On the other hand, the substantial increase in solubility of the composition of the invention as compared with thymidine itself is greater than might be expected by any simple physical effects.

The precise ratio between the thymidine and the solubilizing agent is not critical to the invention and the presence of any quantity of solubilizing agent will have some beneficial effect upon solubility. Moreover, at least to some extent, the solubility of the composition increases as the content of solubilizing agent increases. Thus, too low a content of solubilizing agent has negligible solubilizing effect. On the other hand, if the amount of solubilizing agent is too great, this necessitates the administration to the patient of large quantities of a material which, at best, is neutral or of no therapeutic effect. For this reason, it is good practice to minimise the quantity of solubilizing agent to an extent consistent with achieving the desired solubilizing effect. Thus, for best results in practice, I prefer to use equimolar quantities of the thymidine and the solubilizing agent and, in any case, I prefer that the quantity of solubilizing agent should not be substantially above equimolar, since the greater the proportion of this component, the lower will be the proportion of thymidine available or the activity per unit weight of the composition.

DESCRIPTION OF PREFERRED EMBODIMENTS

The invention is further illustrated by the following Examples, of which Example 1 illustrates a method of preparing sodium p-methyleneaminosalicylate and the remaining Examples illustrate the preparation of the composition of the invention.

EXAMPLE 1

20 g of sodium p-aminosalicylate were dissolved in a mixture of 75 ml of chemically pure ethanol and 150 ml of chemically pure acetone. The air in the reaction vessel was replaced by nitrogen and the reaction vessel was screened from the light. 10 ml of formalin (an aqueous solution containing 35-40% formaldehyde) were then added. The pressure in the reaction vessel was atmospheric and the temperature was ambient (about 25° C.). The materials were allowed to react for about 6 hours, during which time a precipitate formed. At the end of the reaction period, the precipitate was filtered off, washed with small quantities of a 1:2 by volume mixture of ethanol and acetone, and then dried in vacuo, until it was substantially free from solvent. In a series of experiments this drying step required periods ranging from 24 to 28 hours. The product consisted of white crystals, which discoloured when exposed to light and air. The yield was substantially 100% of theory.

EXAMPLE 2

12.1 g (0.05 mole) of thymidine were ground together with 8.6 g (0.05 mole) of sodium p-methyleneaminosalicylate until a fine powdery mixture was obtained. The mixture was stable, provided that it was kept in a tightly closed dark bottle. I found that I could dissolve 1 g of the mixture in a mere 6-7 ml of distilled water (0.1 g thymidine per ml, 0.07 g p-methyleneaminosalicylic acid per ml). Such a solubility will allow the compound to be used in practical therapy, and it was found that the composition had lost substantially none of the thymidine activity.

EXAMPLE 3

1:1 Complex of thymidine and sodium p-methyleneaminosalicylate 1.00 g (4.13 mmole) of thymidine and 0.88 g (4.13 mmole) of sodium p-methyleneaminosalicylate were dissolved in 10 ml of water. The solution was then freeze-dried to give 1.82 g of the desired complex in the form of a light beige, hygroscopic powder.

Elemental analysis—Calculated for $C_{18}H_{20}Na N_3 O_8$: C,47.9%; H,5.0%; N,9.3%. Found: C,48.0%; H,5.4%; N,9.4%.

The water content of the complex was found to be 5.0% by the Karl Fischer method.

0.24 g of the resulting complex (containing approximately 0.127 g of thymidine) dissolved immediately in 1.1 ml of water and the solution remained homogeneous for 16 hours. The solution had a pH value of 7.7.

EXAMPLE 4

1:2 Complex of thymidine and sodium p-methyleneaminosalicylate 1.00 g (4.13 mmole) of thymidine and 1.76 (8.26 mmole) of sodium p-methyleneaminosalicylate were dissolved in 10 ml of water and the solution was freeze-dried to give 2.63 g of the desired complex in the form of a beige, hygroscopic powder.

Elemental analysis—Calculated for $C_{26}H_{26}Na_2 N_4 O_{11}$: C,47.1%; H,4.8%; N,8.4%. Found: C,47.4%; H,4.8%; N,8.5%.

The water content of the resulting complex was 7.1% by weight according to the Karl Fischer method.

0.87 g of the resulting complex (containing approximately 0.32 g of thymidine) dissolved within 10 minutes in 1.1 ml of water and the solution, which had a pH value of 8.1, remained homogeneous for 16 hours.

EXAMPLE 5

1:1 Complex of thymidine and sodium p-aminosalicylate 1.00 g (4.13 mmole) of thymidine and 0.87 g (4.13 mmole) of sodium p-aminosalicylate were dissolved in 10 ml of water and the resulting solution was freeze-dried to give 1.84 g of the desired complex in the form of a white, hygroscopic powder.

Elemental analysis—Calculated for $C_{17} H_{20} Na N_3 O_8$: C,46.0%; H,5.3%; N,9.5%. Found: C,46.1%; H,5.3%; N,9.5%.

The water content of the complex, by the Karl Fischer method, was 6.1% by weight. 0.30 g of this complex (containing approximately 0.16 g of thymidine) dissolved immediately in 1.1 ml of water and the solution remained homogeneous for 16 hours. The solution had a pH value of 7.2.

EXAMPLE 6

1:2 Complex of thymidine and sodium p-aminosalicylate 1.00 g (4.13 mmole) of thymidine and 1.74 g (8.26 mmole) of sodium p-aminosalicylate were dissolved in 10 ml of water and the solution was freeze-dried to give 2.58 g of the desired compound in the form of a white, hygroscopic powder.

Elemental analysis—Calculated for $C_{24} H_{26} Na_2 N_4 O_{11}$: C,45.4%; H,4.9%; N,8.8%. Found: C,45.6%; H,4.9%; N,9.0%.

The water content of this complex by the Karl Fischer method was 6.8% by weight. 1.43 g of the complex (containing about 0.55 g of thymidine) dissolved within 10 minutes in 1.1 ml of water and the solution remained homogeneous for 16 hours. The pH of the solution was 7.6.

Following the procedures described above, a number of complexes of thymidine with different complexing agents were prepared and the results are shown in the following Table, which gives the solubility at 22°–24° C.

TABLE

| complexing agent | complexing agent mole per mole thymidine | thymidine soluble in 100 ml water (g) |
|---|---|---|
|  | 0 | 4.8 ± 0.5 |
| sodium salicylate | 1.06 | 20 ± 1 |
| sodium p-amino-salicylate | 1.00 | 17 ± 1 |
|  | 1.15 | 18 ± 1 |
|  | 1.69 | 45 ± 2 |
|  | 1.84 | 54 ± 2 |
|  | 2.49 | 55 ± 2 |
| sodium p-methylene-aminosalicylate | 1.03 | 12 ± 1 |
|  | 1.36 | 15 ± 1 |
|  | 2.33 | 33 ± 2 |
| sodium p-hydroxybenzoate | 1.43 | 15 ± 1 |
| sodium o-amino-benzoate | 1.50 | 14 ± 1 |
| sodium p-amino-benzoate | 1.60 | 13 ± 1 |
| sodium benzoate | 1.63 | 13 ± 1 |

Plotting the solubility of thymidine against the content of the two complexing agents, sodium p-methyleneaminosalicylate and sodium p-aminosalicylate, gave an S-shaped curve with plateaus at 1 and at 2 moles of complexing agent. This is considered to be evidence for the successive formation of 1:1 and 1:2 complexes with individual solubility properties. At every point in the experiments with aqueous solutions, thymidine and the complexing agent could be identified unchanged.

Various changes and modifications may be made within the purview of this invention, as will be readily apparent to those skilled in the art, such changes and modifications are within the scope and teachings of this invention as defined by the claims appended hereto.

I claim:

1. A solubilized thymidine product having increased solubility in aqueous media comprising thymidine and an amount of a solubilizing agent effective to increase the thymidine solubility in aqueous media, the thymidine solubilizing agent being selected from the group consisting of salicylic acid, its derivatives and salts and esters thereof.

2. A solubilized thymidine product having increased solubility in aqueous media comprising thymidine and an amount of a solubilizing agent selected from the group consisting of methyleneaminosalicylic acid and esters and salts thereof.

3. The product of claim 2 wherein the methyleneaminosalicylic acid is p-methyleneaminosalicylic acid.

4. The product of claim 2 wherein the salts are alkali metal salts.

5. The product of claim 2 wherein the salt is the sodium salt.

6. The product of claim 2 wherein the solubilizing agent is present in about equimolar proportions with the thymidine.

7. An aqueous solution of thymidine containing up to at least about 0.1 gram thymidine per mililiter, the thymidine being present in an amount greater than the normal solubility of thymidine in water and the solution containing a thymidine solubilizing agent effective to increase the thymidine solubility in the aqueous media, the thymidine solubilizing agent being selected from the group consisting of salicylic acid, its derivatives and salts and esters thereof.

8. An aqueous solution of thymidine containing up to at least about 0.1 g thymidine per ml, the thymidine being present in an amount greater than the normal solubility of thymidine in water, the solution containing a solubilizing agent selected from the group consisting of methyleneaminosalicylic acid and esters and salts thereof.

9. The solution of claim 8 wherein the methyleneaminosalicylic acid is p-methyleneaminosalicylic acid.

10. The solution of claim 8 wherein the salts are alkali metal salts.

11. The solution of claim 8 wherein the salt is the sodium salt.

12. The solution of claim 8 wherein the solubilizing agent is present in about equimolar proportions with the thymidine.

13. A method of increasing the solubility of thymidine in aqueous solutions comprising treating thymidine with a thymidine solubilizing agent in an amount effective to increase the aqueous solubility of the thymidine above its normal aqueous solubility and up to at least 0.1 grams thymidine per ml. of water, the thymidine solubilizing agent being selected from the group consisting of salicylic acid, its derivatives and salts and esters thereof.

14. A method of increasing the solubility of thymidine in aqueous solutions comprising treating thymidine with a solubilizing compound in an amount effective to increase the aqueous solubility of the thymidine above its normal aqueous solubility and up to at least 0.1 g thymidine per ml of water, the solubilizing agent being selected from the group consisting of methyleneaminosalicylic acid and esters and salts thereof.

15. The method of claim 14 wherein the methyleneaminosalicylic acid is p-methyleneaminosalicylic acid.

16. The method of claim 14 wherein the salts are alkali metal salts.

17. The method of claim 14 wherein the salt is the sodium salt.

18. The method of claim 14 wherein the solubilizing agent is added to the thymidine in proportions of up to about equimolar proportions with the thymidine.

19. The method of claim 14 wherein the solubilizing compound and thymidine are mixed in the dry state and the treating is conducted by grinding the two products together to form a solubilized thymidine.

* * * * *